United States Patent [19]

Anderson et al.

[11] 4,428,378
[45] Jan. 31, 1984

[54] RATE ADAPTIVE PACER

[75] Inventors: Kenneth M. Anderson, Bloomington; Dennis A. Brumwell, New Brighton, both of Minn.

[73] Assignee: Medtronic, Inc., Minneapolis, Minn.

[21] Appl. No.: 322,815

[22] Filed: Nov. 19, 1981

[51] Int. Cl.³ .............................................. A61N 1/36
[52] U.S. Cl. .............................................. 128/419 PG
[58] Field of Search ....... 128/419 P, 419 PG, 419 PS, 128/419 B

[56] References Cited

U.S. PATENT DOCUMENTS

| | | | |
|---|---|---|---|
| 3,456,134 | 7/1969 | Ko | 128/419 B |
| 3,593,718 | 7/1971 | Krasner et al. | 128/419 PG |
| 3,659,615 | 5/1972 | Enger | 128/419 B |
| 4,140,132 | 2/1979 | Dahl | 128/419 PG |
| 4,164,944 | 8/1979 | Alley et al. | 128/419 PG |
| 4,201,219 | 5/1980 | Gonzalez | 128/419 PG |

FOREIGN PATENT DOCUMENTS 2609365 8/1977 Fed. Rep. of Germany ...... 128/419 PG

OTHER PUBLICATIONS

"Estimating Human Energy Expenditure Using an Accelerometer Device" Servais et al., *IEEE Frontiers of Engineering in Health Care*-1982.
"Effect of Vibrations and Shock on Man" J. T. Broch, Ch5 *Mechanical Vibration and Shock Measurements* Published by Brouel and Kjaer, ® Oct. 1980.

*Primary Examiner*—William E. Kamm
*Assistant Examiner*—Mitchell J. Shein
*Attorney, Agent, or Firm*—Robert C. Beck; John L. Rooney; Joseph F. Breimayer

[57] ABSTRACT

An activity sensor mounted within the pacer detects the general activity level of the patient and alters the escape interval of the pacer between a preset minimum and maximum in response to the detected activity level of the patient.

8 Claims, 4 Drawing Figures

RATE ADAPTIVE PACER

BACKGROUND OF THE INVENTION

1. Field of the Invention

This invention relates to cardiac pacers and more particularly to a rate adaptive pacer which alters the pacing escape interval in response to the physiologic demand of the patient.

2. Description of the Prior Art

Implantable medical devices for the therapeutic stimulation of the heart are well known in the art. Initially these cardiac pacers were asynchronous in operation providing stimulating pulses to the heart at a fixed rate independent of the physiologic demand of the patient.

Subsequently, demand pacemakers were developed as exemplified by U.S. Pat. No. 3,478,746 to Greatbatch. These devices provide stimulating pulses to the heart only in the absence of naturally occurring cardiac activity. This form of pacer permits the patient's underlying cardiac rhythm to inhibit the pacemaker if the patient's intrinsic heart rate is above the preset escape interval of the pacer. However, if the patient's intrinsic cardiac activity drops below the minimum rate set by the escape interval of the pacer, stimulating pulses will be supplied to the heart. In this fashion the demand pacemaker provides a lower boundary rate below which the patient's heart will not be permitted to drop. The therapeutic benefit of such demand pacemakers was enhanced by the development of the hysteresis type pacer known from U.S. Pat. No. RE. 28,003 to Gobeli, which provides two escape intervals.

The hysteresis pacemaker permits the heart to inhibit the pacemaker down to a sentinel rate set by the hysteresis pacemaker. However, if no intrinsic cardiac activity is detected during the sentinel escape interval, the patient's heart will be stimulated at a nominal escape interval which is somewhat shorter than the lower hysteresis rate. In operation, the hysteresis pacer alters the escape interval in response to detected cardiac events.

More recently, pacers have been disclosed which rely upon a historical average of detected cardiac activity to set the escape interval. An example of one such pacer is taught by U.S. Pat. No. 3,921,642 to Preston.

Other forms of rate adaptive pacers have also been proposed. These pacers rely on the sensing of atrial activity, blood PH, respiratory rate and QT interval data to alter the pacer's escape interval. Discussions of some of these prior art proposals may be found in *Relation Between the QT Interval and Heart Rate*, Rickards and Norman, Britt Heart J., 1981; 45; 56–61 and *A Physiologically Controlled Cardiac Pacemaker*, Krasner, Voukydis and Nardella, J.A.A.M.I., Volume I, No. 3, 1966; 14–20.

This historical progression indicates the desire to provide a pacer which alters the escape interval in response to the physiologic demand or needs of the patient.

The structure of the present invention includes a force sensor located within the pacer itself. A prior art example of a related structure is known from U.S. Pat. No. 3,777,762 to Nielsen.

SUMMARY OF THE INVENTION

In contrast to these prior art pacers the present invention provides an activity sensor located within the pacemaker itself to monitor the general level of physical activity of the pacemaker patient. The signal developed from this activity sensor is utilized to alter the escape interval of the pulse generator. In this fashion, the general physical activity of the patient alters the escape interval or demand rate of the pacemaker itself.

Although this invention is disclosed within the context of a single chambered demand pacemaker (VVI), it should be appreciated that the rate adaptive feature based upon the detection of mechanical activity could be applied to any of the currently known pacing modalities including the atrial sequential pacing mode (DVI) and dual demand pacing mode (DDD).

DESCRIPTION OF THE PREFERRED EMBODIMENTS

Figure 1:
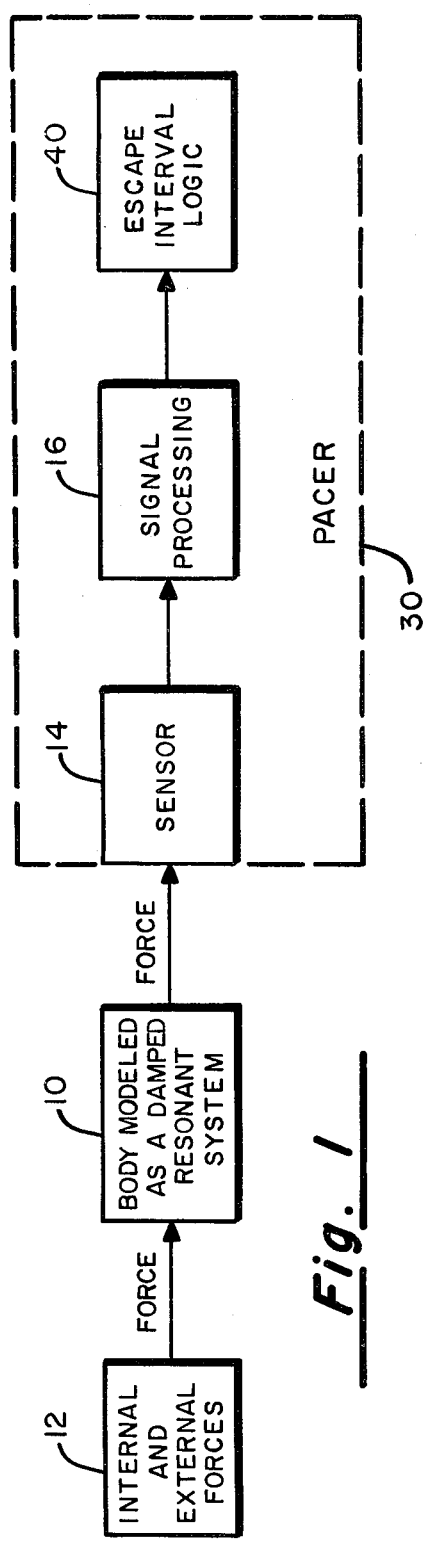
FIG. 1 is a system diagram used for modeling the patient/pacer system.

An understanding of the invention is facilitated by a brief analysis of the patient/pacer system depicted in FIG. 1. In this diagram the patient's body 10 is modeled as a damped resonant system. A variety of mechanical forces both internal and external to the patient are applied to this damped resonant system. These force inputs are modeled by element 12 in the diagram. Forces applied to the body result in forces applied to the sensor 14 contained within the pacer generally designated 30. The raw data from the sensor system 14 is supplied to signal processing circuitry 16 which develops an activity parameter which is applied to alter the escape interval logic 40. The nature of the signal processing circuitry is discussed in connection with FIG. 2.

Data has been collected which shows that the response of the typical human body which results from mechanical activity related to the physical activity of the patient such as pedal impacts from walking or running are centered around approximately 10 Hertz. The sensor 14 located within the pacer interacts with soft tissue at the implant site and detects the various mechanical vibrations present at that location and generates a raw signal. These forces result from the mechanical exertion of the patient which are related to the physiologic demand for oxygenated blood as well as a variety of noise signals resulting from respiration, cardiac activity, speaking and skeletal muscle noise.

Figure 2:
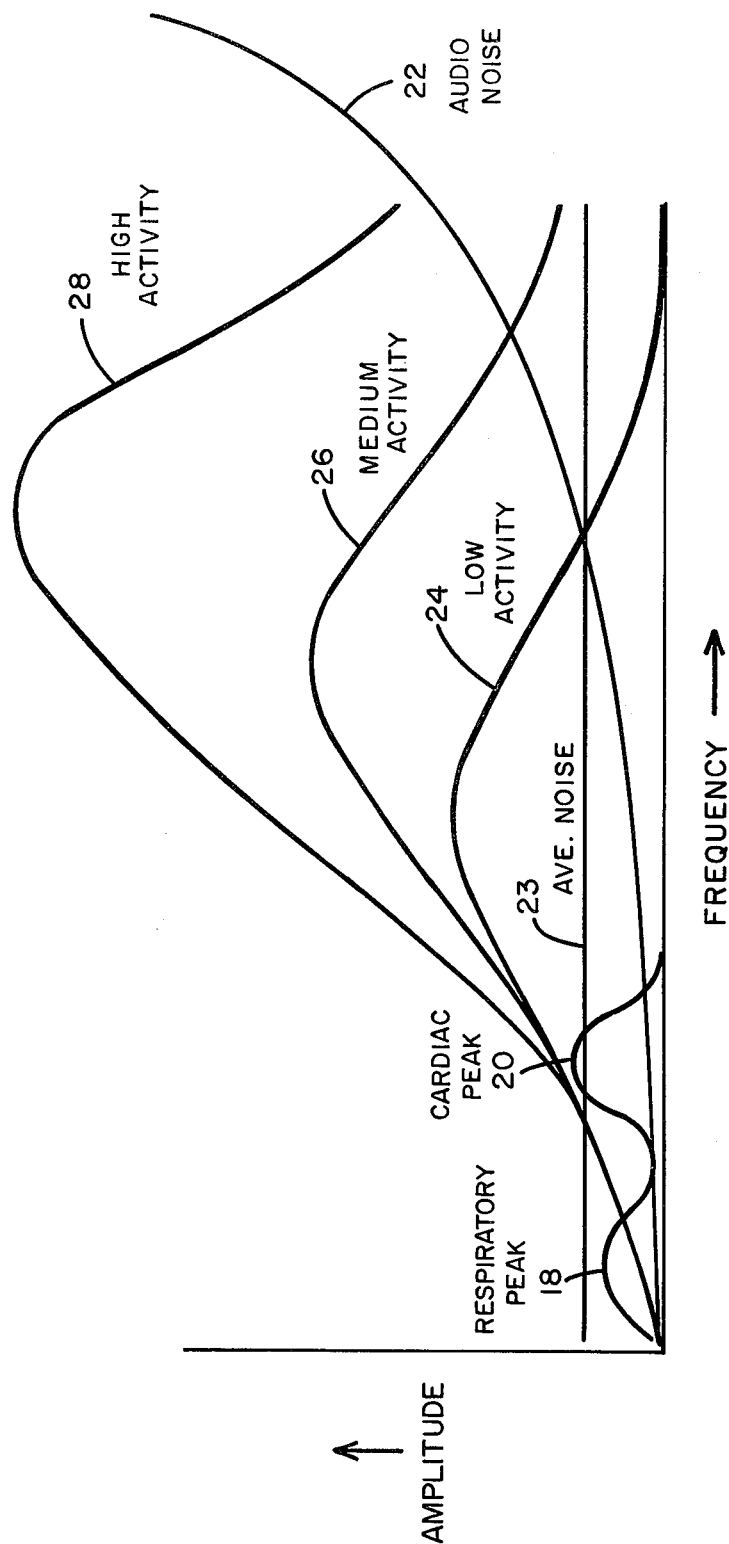
FIG. 2 is a diagram showing the spectral characteristics of the activity signal detected by the sensor as well as the various noise signals present within the patient/pacer system.

In FIG. 2 there is shown a spectral analysis of the electrical raw signal from the sensor. Internal noise due to respiration is centered at approximately 0.2 Hertz while the peak response resulting from cardiac activity is centered at approximately 1.1 Hertz. The amplitude of both of these peaks may lie above the general level of broad-band background noise 23. Noise signals which result from audio signals in the patient's environment as well as noise due to the speech of the patient increase monitonically as shown by curve 22.

The physical activity which will be utilized to alter the escape interval of the pacer is shown by the characteristic activity curves 24, 26 and 28. These curves result from the excitation of the patient's body due to pedal impacts associated with walking and running and correlate strongly with the oxygen demand of the body. It is important to note from the diagram that the curves corresponding with low, medium and high activity all exceed the average noise level 23. It is also important to note that these activity curves lie within a passband which exclude respiratory and cardiac activity as well as the substantial portion of the audio frequency noise 22. The proportionality between the amplitude of these activity curves and the physiologic demand of the patient have been verified through experiment.

Figure 4:
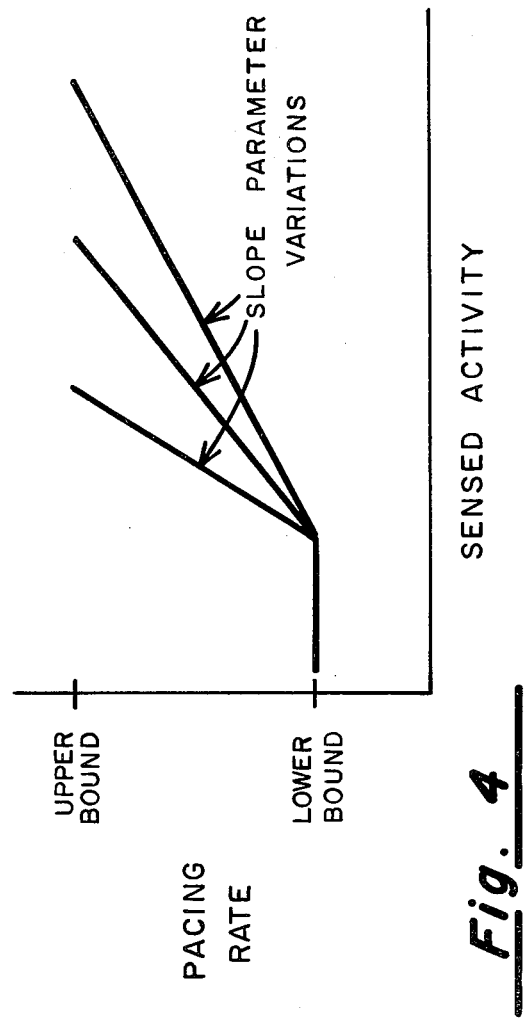
FIG. 4 is a graph depicting the operational mode of the FIG. 3 pacer.

As can be seen from the diagram the spectral peak of the low, medium and high activity curves shifts to the higher frequencies with higher activity levels. It is believed that this phenomena is due to the upward shift of the spectrum of external mechanical excitation. This feature is important with respect to the signal processing parameters selected for the operation of the pacer of the present invention which is described in connection with FIGS. 3 and 4.

Before leaving FIG. 2, it should be clear that the activity signals could be isolated from both high and low frequency noise sources through a filtering process which would attenuate both the respiratory, cardiac and audio components. The amplitude of this signal after bandpass filtration could be used as the activity parameter. However, it is believed that the use of such an activity parameter would be sensitive to the placement of the pacer and would be sensitive to the tissue characteristics surrounding the sensor at the implantation site. In recognition of this effect the invention provides for a zero-crossing detector which effectively tracks the highest amplitude spectral component of the signal present within the passband of the sensor signal. Thus, it is important to note that the signal processing accomplished in block 16 of FIG. 1 first, extracts the activity passband from low frequency cardiac and respiratory noise as well as separating the activity signal from high frequency audio noise. After appropriate bandpass filtration, the sensor signal is passed to a zero-crossing, level detector which rejects all low amplitude signals within the passband. This feature permits the zero-crossing detector to reliably track the spectral peak within the passband.

The level detector is followed by an average zero-crossing rate detector for producing a pulse rate signal proportional to the peak spectral components within the activity passband. This signal is utilized by the pacemaker circuitry for altering the escape interval of the pacer.

This system is capable of extracting a meaningful indication of the physical activity of the patient from a sensor located within the pacemaker can. One application of this sensed activity parameter to a cardiac pacemaker is to utilize the activity parameter to slowly vary the rate between a programmable or preset upper and lower rate. The implementation of such a system is described in connection with FIG. 3.

Figure 3:
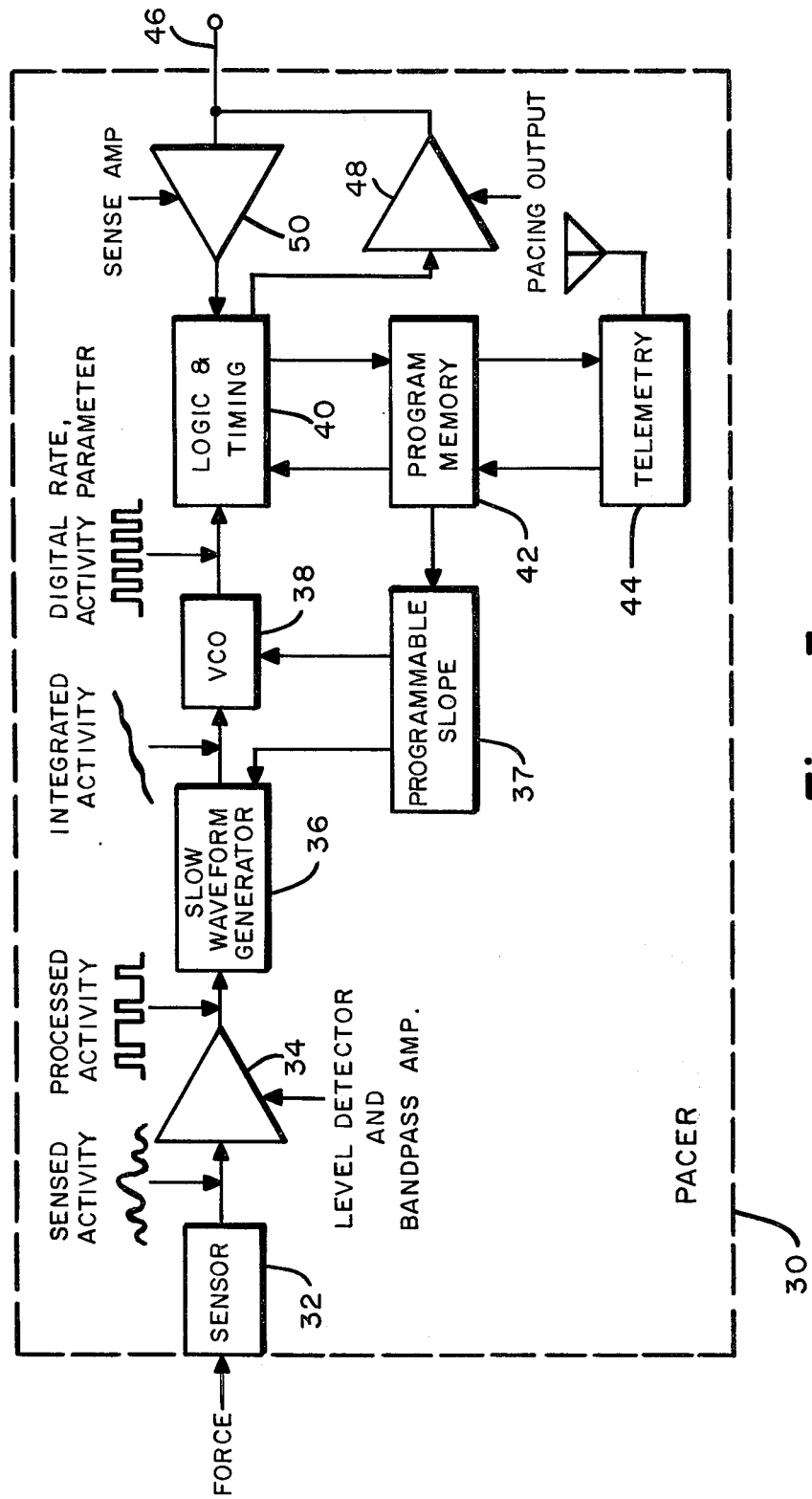
FIG. 3 is a functional block diagram of a single chamber demand pacemaker incorporating the present invention.

In FIG. 3, the pacemaker is designated generally 30. The pacer includes a piezoelectric force sensor 32 coupled to the hermetic enclosure of the pacemaker for converting vibrational energy at the pacemaker site into a sensed activity signal. The sensed activity signal is applied to a bandpass amplifier which rejects the low and high frequency components of the applied force. This signal is also level detected producing a processed activity signal which excludes low amplitude information within the designated passband of the bandpass amplifier. This function is accomplished within circuit element 34. The processed activity signal produced by circuit element 34 is supplied to a slow waveform generator 36 which integrates this activity over a selectable time period selected by programmable slope control 37. The output of the slow waveform generator is applied to the voltage input of a voltage controlled oscillator converting the integrated activity signal into a pulse rate proportional to the magnitude of the activity parameter. This activity parameter signal is supplied to the logic and timing circuitry of a conventional demand pacemaker 40 for altering the escape interval. The details of the implementation of the escape interval alteration circuitry is not provided since they are believed to be within the skill of pacemaker designers.

The escape interval may vary between an upper and lower bound which may be non-invasively programmed through telemetry circuitry 44 and stored within the program memory 42 of the pacemaker. At the end of an escape interval an output stimulus is supplied to the heart through a pacing output amplifier 48 which is coupled to the patient's heart through a lead system 46. Likewise, sensed activity of the heart is detected through a sense amplifier 50 and is supplied to escape interval logic 40 for resetting the escape interval timer in a known fashion. The interaction of the programmable slope circuitry 37 and the slow waveform generator and voltage controlled oscillator are described in connection with FIG. 4. The programmable slope circuitry 37 receives slope parameter information through non-invasive programming of the device. The slope parameter controls how rapidly the pacemaker will move from a lower or preset minimum rate to its maximum or upper rate. When the slope parameter is set at its highest value there will be large increases or changes in the pacemaker's rate with the sensed activity of the patient while the pacemaker rate will change over a small range if this slope parameter is set at its lowest value. This, in essence, controls how rapidly the escape interval of the pacemaker will change in response to sensed activity. Three variations of the slope parameter are shown on the diagram of FIG. 4. When the slope parameter is set at its highest value the pacemaker will respond quickly to the sensed activity of the patient while, when set at its lowest value, the pacemaker will respond slowly to the patient's activity. This parameter permits the physician to control the interaction of the pacemaker with the patient.

What is claimed is:

1. An implantable pacer for the therapeutic stimulation of a patient's heart including a rate variable stimulating system for pacing the heart coupled to a rate determining system for setting the stimulating rate in response to a rate signal dependent on a measured physiologic variable of the patient wherein the improved rate determining system comprises:
    a force transducing sensor producing a raw signal,
    a signal processing means coupled to said force transducing sensor for extracting a rate signal corresponding to the frequency of the highest amplitude component of the bandpassed spectra of said raw signal for generating said rate signal.

2. An implantable pacer for the therapeutic stimulation of a patient's heart including a rate variable stimulating system for pacing the heart coupled to a rate determining system for setting the stimulating rate in response to a rate signal which is dependent on a measured physiologic variable of said patient, wherein the improved rate determining system comprises:

a microphone coupled to said patient responsive to said patient's activity for generating a raw signal, signal processing means coupled to said microphone for generating a rate signal corresponding to the frequency of the highest amplitude component of the bandpass amplified spectra of the raw signal from said microphone means, for generating said rate signal.

3. A variable rate pacer of the type having a rate which is a function of a rate signal, which is dependent on the physical activity of the patient comprising:

a transducer responsive to physical activity generating a raw signal, a bandpass amplifier responsively coupled to said transducer for producing a bandpass filtered signal from said raw signal, detector means responsively coupled to said bandpass amplifier for extracting the highest amplitude spectral component of said bandpass signal, producing an activity signal, slow waveform generator means coupled to said detector means for producing a variable rate signal by integrating said activity signal.

4. The pacer of claim 3 wherein said detector means comprises a zero-crossing level detector means for generating a pulse train of a frequency proportional to the highest amplitude spectral component of said bandpass signal.

5. The pacer of claim 4 wherein said slow waveform generator means comprises analog integrating network means for integrating said pulse train for a selected time interval to generate a rate signal.

6. The pacer of claim 5 further comprising;

a voltage controlled oscillator means, coupled to said slow waveform generator means for generating a digital rate parameter signal proportional to the stimulating rate of said pacer.

7. The pacer of claim 3 wherein said transducer comprises a piezoelectric element bonded to the external enclosure of said pacer for converting vibrational energy at the implant site to an electrical signal.

8. The pacer of claim 3 wherein said bandpass amplifier including means for rejecting low frequency signal components below approximately 1 Hertz and rejects high frequency components above approximately 20 Hertz.

* * * * *